United States Patent [19]

Verdon et al.

[11] Patent Number: 5,063,050

[45] Date of Patent: Nov. 5, 1991

[54] TABLETED POWDER COSMETICS

[75] Inventors: Debra Verdon, Leonardo, N.J.; Marlene Tietjen, New York; Ivonne Brown, Roosevelt, both of N.Y.

[73] Assignee: Revlon, Inc., New York, N.Y.

[21] Appl. No.: 498,298

[22] Filed: Mar. 23, 1990

[51] Int. Cl.$^5$ .................. A61K 7/02; A61K 7/021; A61K 7/035

[52] U.S. Cl. .................. 424/63; 424/DIG. 5; 424/65; 424/69; 424/401; 424/464; 424/465

[58] Field of Search .................. 424/63, 69, DIG. 5, 424/65, 401, 464, 465; 512/2, 4

[56] References Cited

U.S. PATENT DOCUMENTS

| | | | |
|---|---|---|---|
| 3,800,034 | 3/1974 | Kircher et al. | 424/63 |
| 3,978,207 | 8/1976 | Fotiu et al. | 424/63 |
| 4,305,931 | 12/1981 | Kawano et al. | 424/69 |
| 4,323,554 | 4/1982 | Bernhard | 424/69 |
| 4,382,919 | 5/1983 | Alonso et al. | 424/69 |
| 4,407,709 | 10/1983 | Eigen et al. | 424/69 |
| 4,534,963 | 8/1985 | Gordon | 424/69 |
| 4,648,908 | 3/1987 | Takaguka et al. | 424/69 |
| 4,650,672 | 3/1987 | Yagita et al. | 424/69 |

OTHER PUBLICATIONS

The Cosmetic Toiletey and Fragrance Assoc., Cosmetic Ingredient Dictionary, 3/1984, p. 12.

*Primary Examiner*—Dale R. Ore
*Attorney, Agent, or Firm*—Julie Blackburn

[57] ABSTRACT

Cosmetic powder compositions which may be readily compression molded in various shapes are formed from, in weight %,
about 10% to 80% of talc,
about 0.1% to 20% of a powdered lubricant,
about 0.1% to 20% of a powdered sorbent agent, and
about 0.1% to 20% of a liquid binder.

Fillers, colorants, preservatives, antioxidants, binders and other cosmetic powder components may also be used.

8 Claims, No Drawings

TABLETED POWDER COSMETICS

BACKGROUND OF THE INVENTION

1. Field Of The Invention

This invention relates to powdered cosmetic preparations prepared in the form of compressed tablets without the use of a pan. The pressed tablets provide for a more facile use of the powdered cosmetic, that is, without any of the disadvantages resulting from the use of the cosmetic in loose powder form, e.g., messiness, loss of powder by spilling, and other known disadvantages.

The cosmetic formulations of the present invention have good pay-off and would include those commonly used as cheek rouge, face powders, blushes, eye shadow, highlighter, and others such as fragrance bead or deodorant powder.

2. Description of the Prior Art

The prior art has disclosed the preparation of powdered compressed cosmetics which require the use of special components and/or processing aids or conditions.

U.S. Pat. No. 3,800,034 discloses the preparation of sticks of pressed cosmetic powder which contain 40 to 90% chalk.

U.S. Pat. No. 3,978,207 discloses the preparation of pressed cosmetics having a frosted pearl effect and which contain about 30–90% of a nacreous material such as mica, bismuth oxychloride or mica coated with titanium dioxide or bismuth oxychloride.

U.S. Pat. No. 4,305,931 requires the presence of a hydroxypropyl-etherified glycolipid ester to prevent cracking if the compressed powder is dropped or dried.

U.S. Pat. Nos. 4,358,286, 4,459,285, 4,569,839, 4,581,230 and 4,767,618 disclose, in part, the preparation of various cosmetic preparations containing pulverized particles of flowers or plants with certain thickening agents.

U.S Pat. No. 4,534,963 discloses high pearlescent pressed powder eye shadow compositions made with 40-80% of nacreous material and other components such as micronized polyethylene wax and certain tetraesters.

U.S. Pat. Nos. 4,591,502 and 4,609,545 disclose the use of certain hydrocarbon waxes as compressing aids for cosmetic powders.

U.S. Pat No. 4,650,672 discloses a multicolored pressed cosmetic powder formed from grains of various pigments.

U.S. Pat. No. 4,659,562 discloses the use of an admixture of finely divided silica and finely divided polyethylene fibers as a binding agent for certain cosmetic formulations.

U.S. Pat. No. 4,724,138 discloses the use of calcium sulfate hemihydrate in the formation of a shaped pigmented cosmetic powder.

U.S. Pat. No. 4,772,331 discloses the use of colored flaky pigment compositions in cosmetics.

U.S. Pat. No. 4,783,333 discloses the use of stones or pearls of color coated titanated mica particles for eye shadow or blusher formulations.

It is an object of the present invention is to provide pressed cosmetic powders without the use of an aqueous medium or a molding pan.

A further object of the present invention is to provide a pressed cosmetic powder having good pay-off properties.

A further object of the present invention is to provide a kit of several different pressed cosmetic powders having various colors so that the users can blend such colors to obtain personally desired shades and mixtures of such colors.

SUMMARY OF THE INVENTION

These and other objects are attained by a novel pressed cosmetic powder composition formed from, in percent by weight, about 10–80%, and preferably about 10 to 65%, of talc,
about 0.1 to 20%, and preferably about 1 to 10%, of a powdered lubricant,
about 0.1 to 20%, and preferably about 1 to 10%, of a powdered sorbent agent, and
about 0.1 to 20%, and preferably about 1 to 6%, of a liquid binder.

DETAILED DESCRIPTION OF THE INVENTION

The talc which is useful in the present invention is a cosmetic grade of talc. Talc is a natural hydrous magnesium silicate. Such talc is essentially a white, odorless, fine powder ground from a naturally occurring rock ore and it typically consists of about 90% hydrous magnesium silicate having a structural formula of $Mg_6(Si_8O_{20})$-$(OH)_4$ with the remainder consisting of naturally associated minerals such as calcite, chlorite, dolomite, kaolin and magnesite and containing no asbestos minerals.

Aluminum starch octenylsuccinate is preferred as a powdered lubricant. While preferred, other powdered lubricants can be added or substituted, for the aluminum starch octenylsuccinate. These include teflon, L-laureth lycine, polyethylene, nylon, boron nitride, polymethylmethacrylate (PMMA), spherical silica, metallic stearates (including zinc stearate, aluminum stearate, magnesium stearate, potassium stearate, calcium stearate and lithium stearate), starch cellulose, and kaolin.

Calcium silicate serves as the preferred powdered absorber or sorbent agent. While calcium silicate is preferred, other sorbent agents which can be added or substituted for the calcium silicate include silica and the sodium, magnesium and aluminum silicates. Bentonite, organo modified bentonite, hectorite, kaolinate, dicite, nacrite, metahalloysite, pyrophyllite, and montmorillonite may also be used.

The liquid binder can be lanolin, lanolin alcohol, mineral oil and mixtures thereof. While these liquid binders are preferred other "oil" binders can be used. These include any of the mineral oils, liquid long chain alcohols (oleyl alcohol), liquid esters of long chain fatty acids (isocetyl stearate and isopropyl myristate) and liquid esters of long chain alcohols (hexadecyl adipate). These and other liquid oils shown on pages 80 and 81 under the Heading "Skin Conditions Agents-Emollients" of the *CTFA Cosmetic Ingredient Dictionary*, Third Edition or Third Edition Supplement, published by the Cosmetic, Toiletry and Fragrance Association, Inc., Washington, D.C. These pages of the dictionary volumes, published 1982 and 1985, respectively, are incorporated herein by reference. A preferred liquid binder utilizes an admixture of lanolin alcohol and mineral oil in a weight ratio to each other of about 10 to 90.

The compositions may also contain
about 1 to 10%, and preferably about 1 to 5%, bismuth oxychloride (BiOCl)

about 10 to 80%, and preferably about 20 to 50%, of one or more fillers such as mica, sercite, $TiO_2$ coated mica, bronze or copper powders, aluminum powders or zinc oxide, about 0.0 to 40%, and preferably about 0 to 20%, of one or more coloring agents for cosmetic powders. All colors listed on pages 62 and 63 of the above-mentioned *CTFA Cosmetic Ingredient Dictionary* can be used.

The pressed powders can be prepared and sold in various shapes and/or containers, such as in the form of sticks, compacts, tablets, pellets.

The shaped products can be marketed individually, e.g., as a single colored product, or they can be marketed in kit form, wherein a plurality of different colored shaped products are included. Whether the variously colored products are obtained individually or in kit form, the user can personally blend the colors to obtain a desired color blend.

The powders in their pressed form may be applied to the skin of the user directly, as when used in the form of a stick, or by the use of a puff or other applicator. These pressed powders have a firm consistency but maintain good even pay off when applied to the skin and without the dusting problems that can arise when using loose powders.

The talc particles are selected so as to provide translucency and silkiness to the final product. The BiOCl provides the product with smooth even application characteristics without interfering with the color laydown. The metal stearates aid in the wear of the product on the skin and act as binders. The aluminum starch octenylsuccinate helps in providing the final product with creaminess and good payoff characteristics. The lanolin alcohol and/or mineral oil serve as emollients and a liquid binder.

The fillers provide sheen and brilliance to the colors and help to maintain uniformity of color from shade to shade of color. The calcium silicate aids in the absorption of excess oils and thus helps to maintain color trueness. It also aids in the pressability of the powders without hurting payoff from the pressed tablet. The antioxidants prevent rancidity in the oils that are used.

The pressed powder products, when applied to the skin, provide a creamy texture, a moisturizing effect and a light sheer coverage. They provide for an even smooth application to the skin and provide longer wear and maintain color trueness. When used in bronze colored form, these cosmetics are, particularly, less dusty than prior art loose bronze powders. The pressed powders of this invention can be used to provide a range of color patterns from a translucent glow to a bold color laydown.

The compressed powder product may be made by mixing or blending the powders until uniform in a Gemco, Patterson Kelley, Littleford or Ribbon blender. Oils are added in a conventional manner through input devices of related equipment. The product is then pre-compacted to reduce compression ratio in the final press to between a 2:1 to 4:1 ratio (as is known in the pharmaceutical industry).

The blended powders are then compressed together without the need for a molding pan into the shapes desired for marketing purposes, such as spheres, cones, hearts, pillows, cubes, etc., by using conventional tablet pressing equipment and techniques commonly used in the pharmaceutical industry.

The following examples are merely illustrative of the scope of the present invention and are not intended as a limitation thereon.

EXAMPLE

Several formulations were prepared and pressed into the shape of pellets. These formulations are the following, in parts by weight:

| Parts By Weight Component | Formula I Medium Bronze Colored | Formula II Light Bronze Colored | Formula III Gold Deep Bronze Colored | Fragrance |
|---|---|---|---|---|
| Talc | 46.45 | 56.35 | 16.95 | 28.45 |
| BiOCl | 5.00 | 2.00 | 2.00 | 5.00 |
| Zn Stearate | 6.00 | 3.00 | 10.00 | 6.50 |
| Al Starch Octenyl | 1.00 | 4.00 | 6.00 | 3.50 |
| Mica | 10.00 | — | — | 43.00 |
| Ca Silicate | 10.00 | 1.00 | 6.00 | 4.80 |
| Phenoxyethanol | 1.00 | 1.00 | 1.00 | 0.70 |
| Lanolin Alcohol | 0.20 | — | 0.60 | 0.70 |
| Mineral Oil | 1.80 | — | 5.40 | 0.10 |
| Isocetyl Stearate | — | 5.00 | — | 0.90 |
| BHA | 0.005 | 0.05 | 0.05 | 0.05 |
| I/O Red | 5.00 | 1.00 | — | — |
| I/O Black | 1.50 | 0.50 | — | — |
| I/O Maroon | 5.00 | 0.20 | — | — |
| Ultramarine Blue | — | 0.70 | — | — |
| I/O Yellow | 7.00 | 0.20 | 2.00 | — |
| Yellow #5 Al Lake | | | | |
| $TiO_2$/Mica | — | 25.00 | 50.00 | — |
| Fragrance | — | — | — | 5.00 |
| TOTAL | 100.00 | 100.00 | 100.00 | 100.00 |

While this invention has been described by reference to specific examples, it is intended to be limited only by the scope of the appended claims.

What is claimed is:

1. A cosmetic powder composition compression molded into a pressed tablet form at a compression ratio of between 2:1 to 4:1, comprising, in percent by weight:
    about 10 to 80% talc,
    about 0.1 to 20% aluminum starch octenylsuccinate
    about 0.1 to 20% of a powdered sorbent agent selected from the group consisting of calcium silicate, silica, sodium silicate, magnesium silicate, aluminum silicate, bentonite, organomodified bentonite, hectorite, kaolinite, diate, nacrite, metahalloysite, pyrophyllite, and montmorillonite, and
    about 0.1 to 20% of a liquid binder.

2. The cosmetic powder of claim 1 wherein the powdered lubricant is aluminum starch octenyl succinate, and the powdered sorbent agent is calcium silicate.

3. A cosmetic powder as in claim 2 further comprising
    about 0.0 to 10% of bismuth oxychloride,
    about 0.1 to 20% of one or more metal stearates,
    about 10 to 80% of one or more fillers,
    about 0.01 to 0.10% of one or more antioxidants,
    about 0 to 40% of one or more coloring agents, and
    about 0 to 10% of one or more fragrances.

4. A cosmetic powder composition compression molded at a compression ratio of between 2:1 to 4.1 comprising, in percent by weight,
    about 10 to 65% of talc, about 1 to 10% of aluminum starch octenylsuccinate,
about 1 to 10% of calcium silicate, and
about 1 to 6% of a liquid binder.

5. The cosmetic powder of claim 4 wherein the liquid binder is lanolin, lanolin alcohol, mineral oil and mixtures thereof.

6. A cosmetic powder as in claim 4 further comprising
about 1 to 5% of bismuth oxychloride,
about 4 to 8% of one or more metal stearates,
about 20 to 50% of one or more fillers,
about 0.01 to 0.05% of one or more antioxidants and
about 0 to 20% of one or more coloring agents.

7. A cosmetic composition as in claim 5 which is bronze colored.

8. A cosmetic composition as in any one of claims 1 to 7 which is a face powder, cheek rouge, blush, eye shadow, highlighter, fragrance bead or deodorant powder.

* * * * *